US 6,699,286 B2

(12) United States Patent
Sklar

(10) Patent No.: US 6,699,286 B2
(45) Date of Patent: Mar. 2, 2004

(54) METHOD AND APPARATUS FOR MAKING A LIGAMENT REPAIR USING COMPRESSED TENDONS

(76) Inventor: Joseph H. Sklar, 210 Park Dr., Longmeadow, MA (US) 01106

( * ) Notice: Subject to any disclaimer, the term of this patent is extended or adjusted under 35 U.S.C. 154(b) by 0 days.

(21) Appl. No.: 09/864,848

(22) Filed: May 24, 2001

(65) Prior Publication Data

US 2002/0013623 A1 Jan. 31, 2002

Related U.S. Application Data

(60) Provisional application No. 60/206,682, filed on May 24, 2000.

(51) Int. Cl.[7] .................................................. A61F 2/08
(52) U.S. Cl. ..................... 623/13.17; 623/915; 623/901; 606/36
(58) Field of Search .................. 623/11.11, 13.11–13.2, 623/901, 915, 917, 23.72–23.76, 17.12; 600/36

(56) References Cited

U.S. PATENT DOCUMENTS

| | | | |
|---|---|---|---|
| 5,329,846 A | * | 7/1994 | Bonutti .................... 100/162 B |
| 5,397,357 A | * | 3/1995 | Schmieding et al. ......... 606/86 |
| 5,403,317 A | | 4/1995 | Bonutti |
| 5,425,762 A | * | 6/1995 | Muller .................... 623/11.11 |
| 5,800,544 A | | 9/1998 | Demopulos et al. |
| 5,829,323 A | | 11/1998 | Liston |
| 6,143,029 A | | 11/2000 | Rippstein |
| 6,159,217 A | | 12/2000 | Robie et al. |
| 6,371,984 B1 | * | 4/2002 | Van Dyke et al. ......... 623/11.11 |

FOREIGN PATENT DOCUMENTS

WO  WO 97/33535 A1  9/1997

* cited by examiner

*Primary Examiner*—David J. Isabella
*Assistant Examiner*—Urmi Chattopadhyay
(74) *Attorney, Agent, or Firm*—Pandiscio & Pandiscio

(57) ABSTRACT

A method and apparatus of making repairs with graft ligaments. In one form, the method for graft ligament reconstruction comprises (i) harvesting a graft ligament consisting entirely of soft tissue; (ii) compacting the graft ligament through compression so as to significantly reduce the cross-sectional area and increase the density of the collagen material of the graft ligament; and (iii) deploying the compressed graft ligament in the human body. In another form, the apparatus for graft ligament reconstruction comprises a graft ligament having a given diameter and a given cross-sectional area; and a compacting instrument having at least one surface to contact the graft ligament and to decrease the given cross-sectional area of the graft ligament to a reduced cross-sectional area, whereby the graft ligament with the decreased cross-sectional area may be positioned within a bone tunnel having a cross-sectional area smaller than the given cross-sectional area of the graft ligament in its original state.

16 Claims, 11 Drawing Sheets

"NORMAL" GRAFT LIGAMENT → COMPACTED GRAFT LIGAMENT

METHOD AND APPARATUS FOR MAKING A LIGAMENT REPAIR USING COMPRESSED TENDONS

REFERENCE TO PENDING PRIOR PATENT APPLICATION

This patent application claims benefit of pending prior U.S. Provisional Patent application Ser. No. 60/206,682, filed May 24, 2000 by Joseph H. Sklar for METHOD AND APPARATUS FOR MAKING AN ACL REPAIR USING DEHYDRATED TENDONS (Attorney's Docket No. SKLAR-23 PROV), which patent application is hereby incorporated herein by reference.

FIELD OF THE INVENTION

This invention relates to surgical methods and apparatus in general, and more particularly to methods and apparatus for making an ACL repair.

BACKGROUND OF THE INVENTION

A ligament is a piece of fibrous tissue which connects one bone to another.

Ligaments are frequently damaged (e.g., detached or torn or ruptured, etc.) as the result of injury and/or accident. A damaged ligament can impede proper motion of a joint and cause pain.

Various procedures have been developed to repair or replace a damaged ligament. The specific procedures used depend on the particular ligament which is to be restored and the nature and extent of the damage.

One ligament which is frequently damaged as the result of injury and/or accident is the anterior cruciate ligament (ACL). Looking now at FIG. 1, an ACL 5 is shown extending between the top of the tibia 10 and the bottom of the femur 15. A damaged ACL 5 can cause instability of the knee joint, further damage to other structures, and cause substantial pain and arthritis.

Numerous procedures have been developed to restore a damaged ACL through a graft ligament replacement. In general, these ACL replacement procedures involve drilling a bone tunnel 20 (FIG. 2) through tibia 10 and up into femur 15. Then a graft ligament 25, consisting of a harvested or artificial ligament or tendon, is passed through tibial tunnel 30, across the interior of the joint, and up into the femoral tunnel 35. Then a distal portion of graft ligament 25 is secured in femoral tunnel 35 and a proximal portion of graft ligament 25 is secured in tibial tunnel 30.

There are currently a variety of ways to secure graft ligament 25 in a bone tunnel. One way is to use an interference screw 40 (FIG. 3), such as the ARTHREX interference screw, to "directly" wedge graft ligament 25 against the side wall of bone tunnel 20. Another way is to use a bearing structure and expansion screw 45 (FIG. 4), such as the INNOVASIVE INTRAFIX system, to "indirectly" wedge graft ligament 25 against the side wall of the bone tunnel 20. Still another way is to use a fastener device 50 (FIG. 5), such as the INNOVASIVE LYNX system, to secure graft ligament 25 in bone tunnel 20. Yet another way is to use an anchor 55 (FIG. 6), such as the MITEK ligament anchor, to suspend graft ligament 25 within bone tunnel 20. And another way is to use a suture suspension system 60 (FIG. 7), such as the ACUFEX ENDOBUTTON system, to suspend graft ligament 25 in bone tunnel 20. And still another way is to use a cross-pinning system 65 (FIG. 8), such as the ARTHREX cross-pinning system, to suspend graft ligament 25 in bone tunnel 20. And yet another way is to pass graft ligament 25 completely through bone tunnel 20 and affix graft ligament 25 to the outside of the bone with a screw and washer arrangement 70 (FIG. 9) or a staple (not shown).

Some of the aforementioned reconstruction techniques utilize a graft ligament which is harvested so as to include a portion of bone block, e.g., a patellar tendon including a portion of the patella. Others of the aforementioned reconstruction techniques utilize a graft ligament which is harvested so as to consist entirely of soft tissue, e.g., a harvested hamstring tendon.

In general, it is preferable to harvest graft ligaments consisting entirely of soft tissue, e.g., a hamstring tendon, since this involves less trauma to the donor site. However, graft ligaments consisting entirely of soft tissue are more difficult to biologically integrate into the host bone, due to the fact that two different types of tissue are involved, i.e., both tendon and bone. Such difficulties with biological integration can raise questions as to the adequacy and permanence of the ligament reconstruction. As a result, many ligament reconstructions are still effected using a graft ligament which includes a portion of bone block. While such "bone block" reconstructions generally result in more significant trauma to the donor site, they also simplify biological integration of the graft ligament into the host bone since, within a bone tunnel, bone heals to bone more readily than tendon heals to bone.

In addition to the foregoing, ligament reconstructions tend to be complex surgical procedures where a variety of factors must be carefully balanced in order to achieve the best possible results. More particularly, in order to optimize the ligament reconstruction and minimize trauma to the surrounding anatomy, it is generally necessary to position a sizable graft ligament at exactly the right location within the joint, taking care to minimize trauma to the host bones by making the smallest possible bone tunnels. More particularly, when creating the ligament reconstruction, it is generally important to use as much graft ligament material as possible, so as to (i) provide the highest possible graft strength along the length of the graft, whereby to prevent subsequent rupture, and (ii) provide an extensive supply of collagen material, whereby to facilitate effective integration of the graft ligament into the bone. At the same time, the physics of the knee joint dictate the location of the graft ligament and hence the location of the bone tunnels, and the particulars of the surrounding anatomy may effect graft ligament size and/or bone tunnel size. And in addition to the foregoing, it is also generally important to minimize the size of the bone tunnels. Minimizing the size of the bone tunnels is important, since (i) larger bone tunnels are more destructive of the host bone, (ii) larger bone tunnels are more difficult to revise later on in the event of graft failure, and (iii) larger bone tunnels have larger diameters and, since bony ingrowth commences from the periphery of the bone tunnel, may reduce the proportion of tendon experiencing bony ingrowth, thereby weakening graft fixation. Thus it will be seen that the relative sizing of the graft ligament and the bone tunnels is a delicate balance involving a range of factors.

In addition to all of the foregoing, there must also be sufficient clearance between the graft ligament and the walls of the bone tunnels to permit the graft ligament to be pushed and/or pulled into position within the bone tunnels. And to further complicate the matter, in many cases, the surgeon must also be able to position surgical instruments within the bone tunnels, alongside the/graft ligament. Thus, "real estate" becomes a very precious commodity in ligament reconstructions. In practice, in order to permit deployment of the graft ligament within the bone tunnel, the graft ligament must generally be sized so as to have a cross-sectional area at least somewhat less, and in some cases significantly less, than the cross-sectional area of the bone tunnels it is to be deployed in.

Unfortunately, there are at least three significant problems associated with "undersizing" the graft ligament relative to the bone tunnel. First, such undersizing tends to undermine biological integration of the graft ligament with the host bone. Second, it can allow some movement of the graft ligament to occur relative to the host bone. Such movement can further impede the aforementioned biological integration; in addition, it can also result in abrasion, and hence deterioration, of the graft ligament and/or the host bone. Third, undersizing of the graft ligament relative to the host bone tunnel can also permit the incursion of synovial fluid into the bone tunnel. Such synovial fluid incursion is believed to result in degradation of the bone tunnel and/or in degradation of the biological integration of the graft ligament into the host bone.

SUMMARY OF THE INVENTION

As a result, one object of the present invention is to provide an improved way of effecting a ligament reconstruction using graft ligaments consisting entirely of soft tissue, yet which facilitates effective biological integration of the graft ligament with the host bone.

Another object of the present invention is to provide a way to temporarily reduce the size of the graft ligament so as to facilitate easy deployment of the graft ligament in the bone tunnels, while still permitting the graft ligament to return to its normal size so as to be sized more closely to the size of the bone tunnel and thereby eliminate the "undersizing" problems referred to above.

These and other objects are addressed by the provision and use of the present invention, which comprises a new procedure for graft ligament reconstruction. The procedure involves the following steps (i) harvesting a graft ligament consisting entirely of soft tissue, e.g., a hamstring tendon; (ii) compacting the tendon through compression, so as to significantly reduce its cross-sectional area and increase the density of its collagen material; and (iii) deploying the compressed tendon in the body, using the reconstruction technique of choice. Compacting can be effected using a variety of instruments, e.g., squeezing pliers, hinged plates, a conical tube, etc.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

The present invention provides a new procedure for graft ligament reconstruction. The procedure involves the following steps:

(i) harvesting a graft ligament consisting entirely of soft tissue, e.g., a hamstring tendon;

(ii) compacting the tendon through compression, so as to significantly reduce its cross-sectional area and increase the density of its collagen material; and (iii) deploying the compressed tendon in the knee, using the reconstruction technique of choice.

Compaction generally acts to reduce the volume of fluid within the graft ligament, whereby to reduce the volume of the graft ligament.

Figure 1:
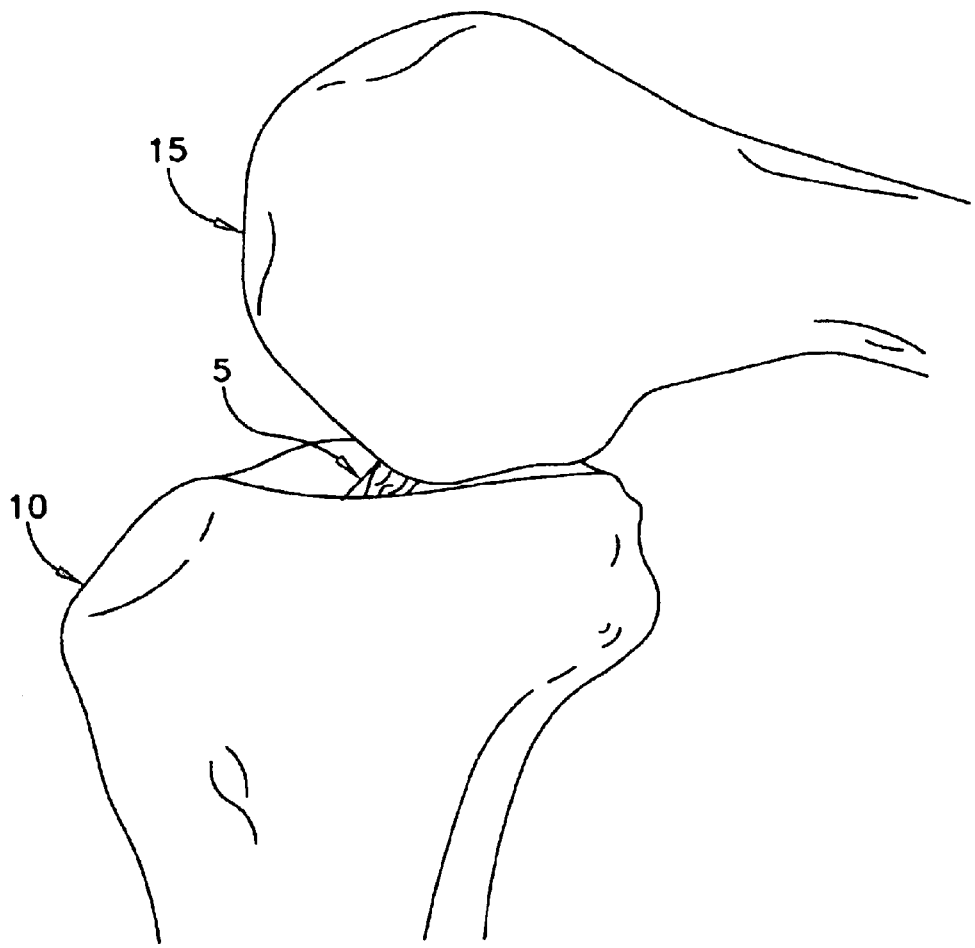
FIG. 1 is a schematic side elevational view of a knee joint showing a ACL extending between the tibia and the femur.
Figure 2:
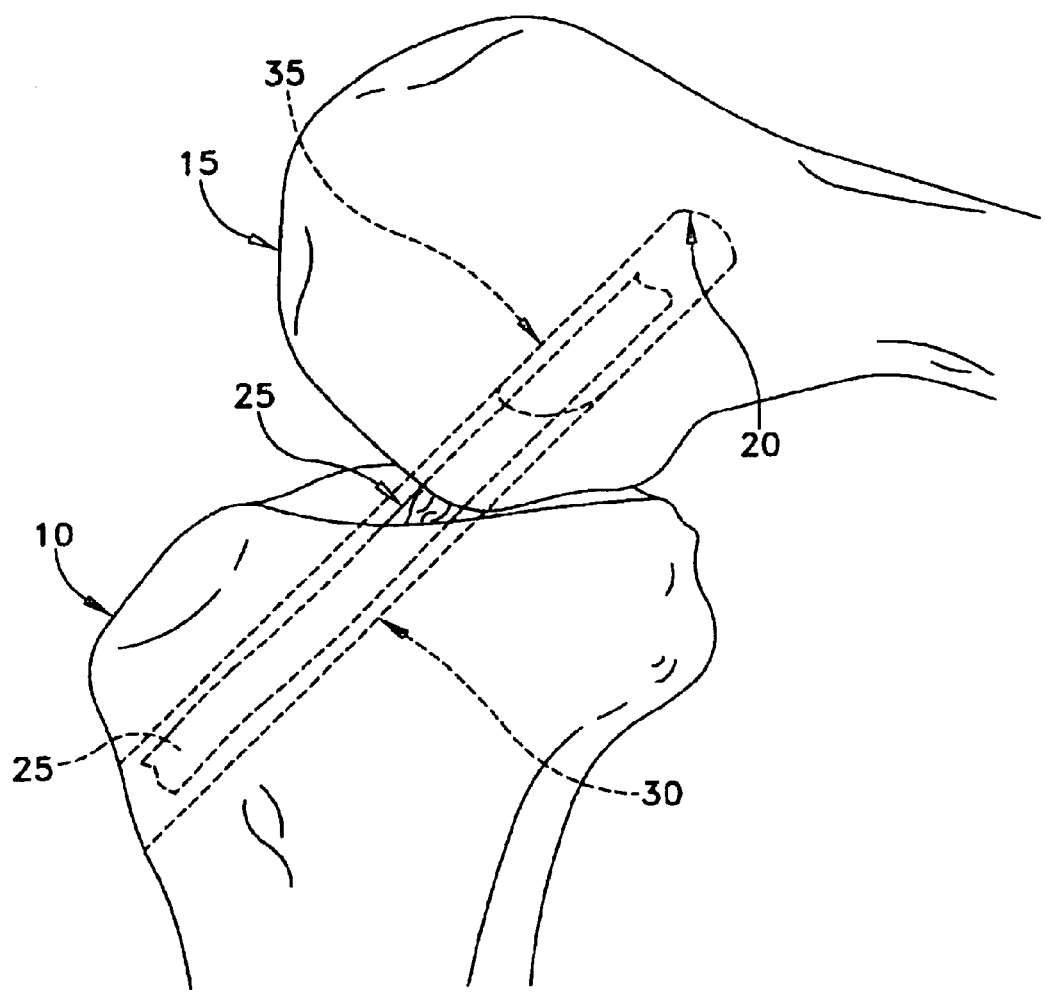
FIG. 2 is a schematic side elevational view of a knee joint showing a graft ligament extending between the tibia and the femur.
Figure 3:
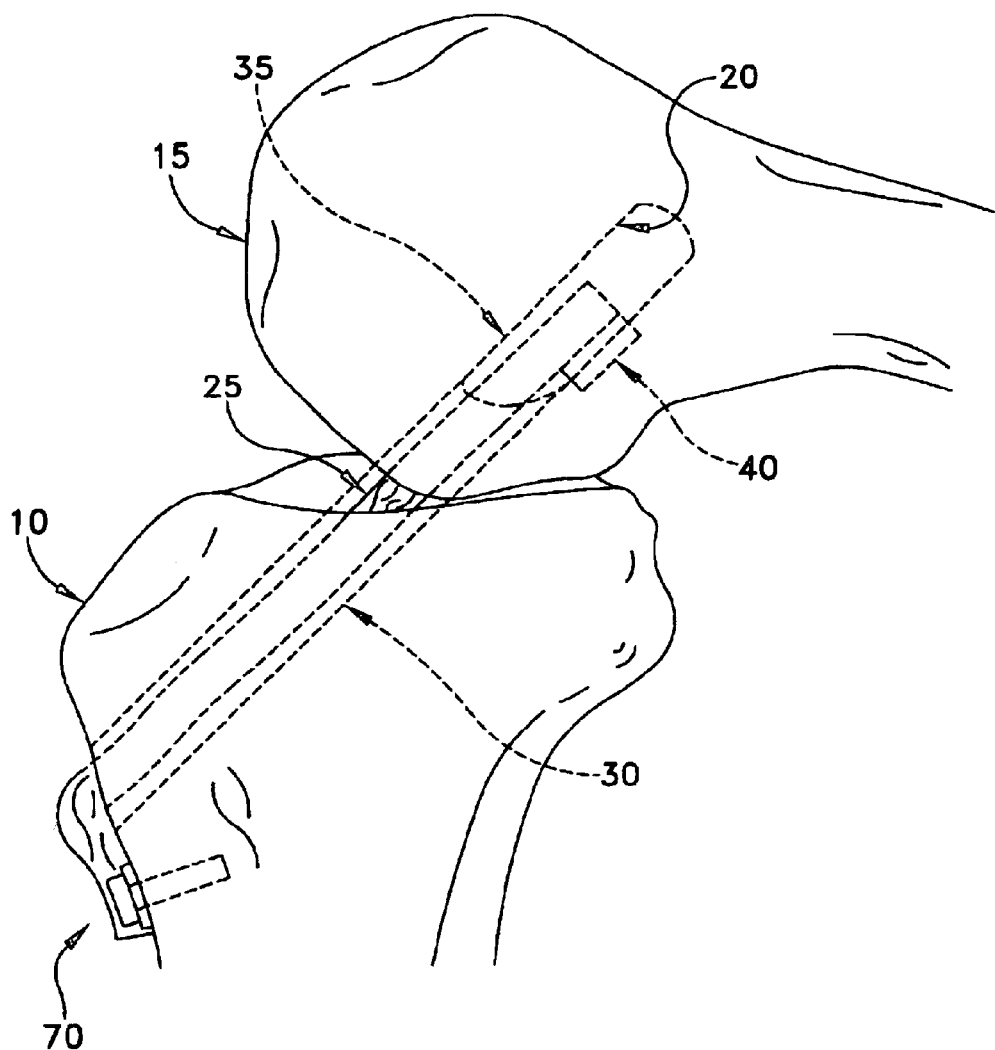
FIG. 3 is a schematic side elevational view showing a graft ligament secured in a bone tunnel by an interference screw.
Figure 4:
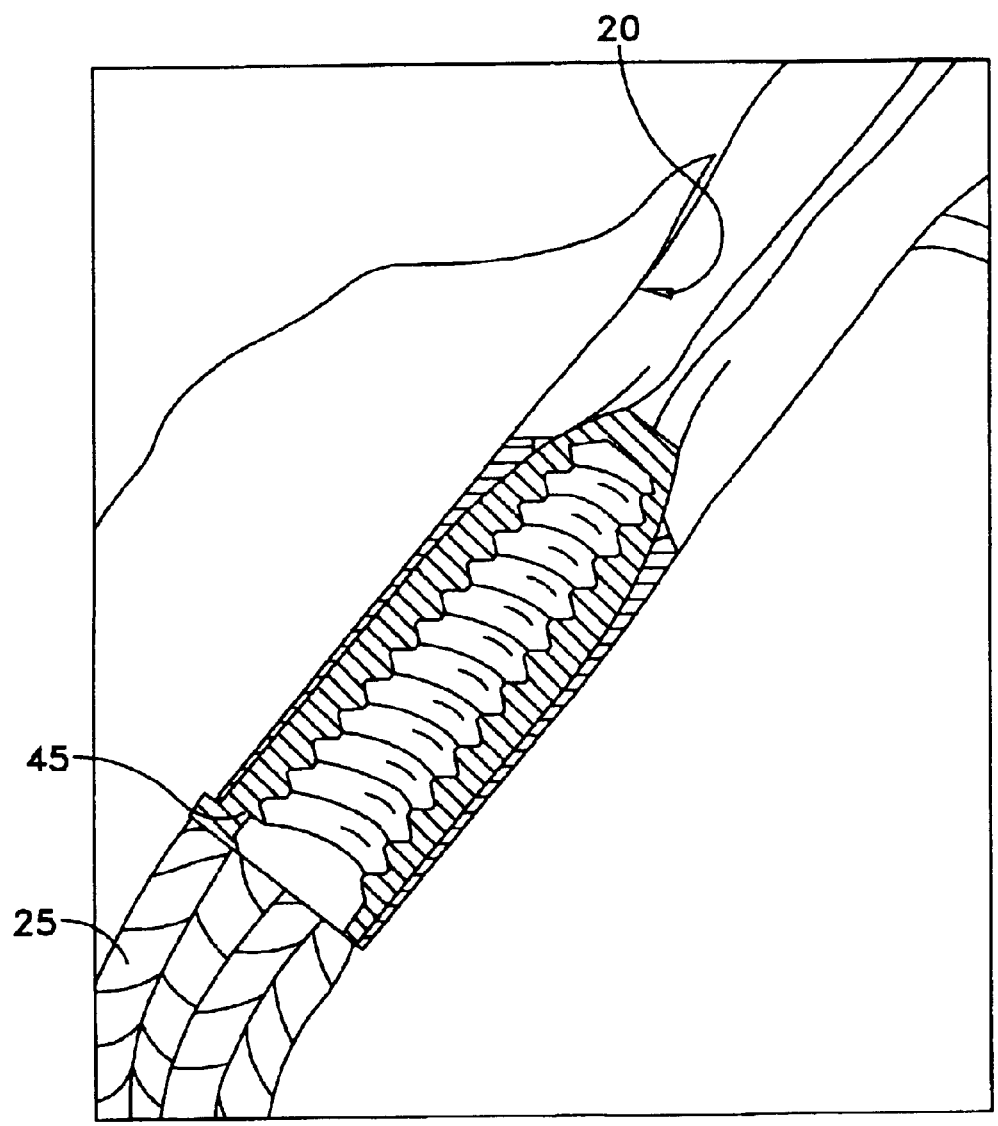
FIG. 4 is a schematic side elevational view showing a graft ligament secured in a bone tunnel by a bearing structure and expansion screw.
Figure 5:
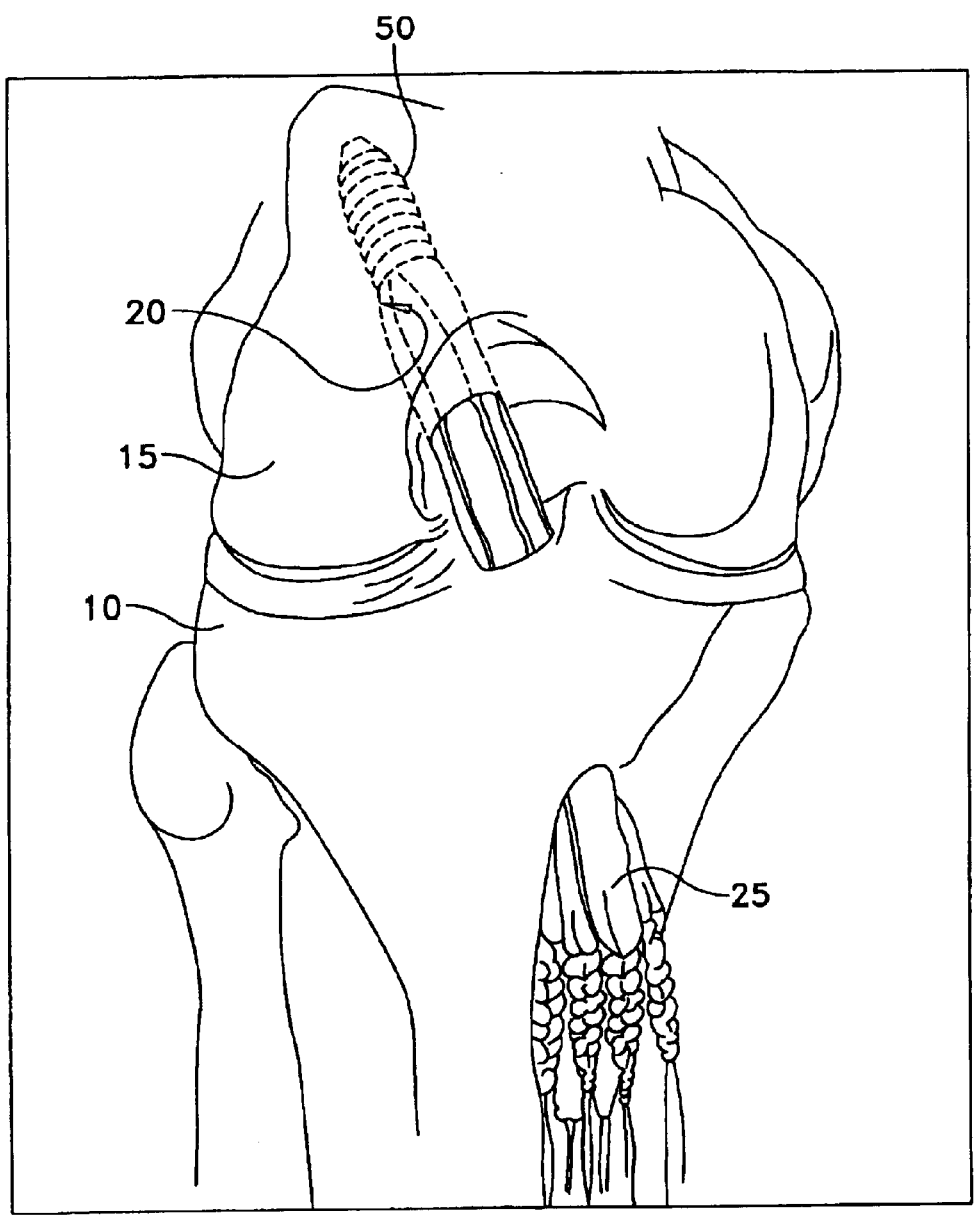
FIG. 5 is a schematic side elevational view showing a graft ligament secured in a bone tunnel by a fastener device.
Figure 6:
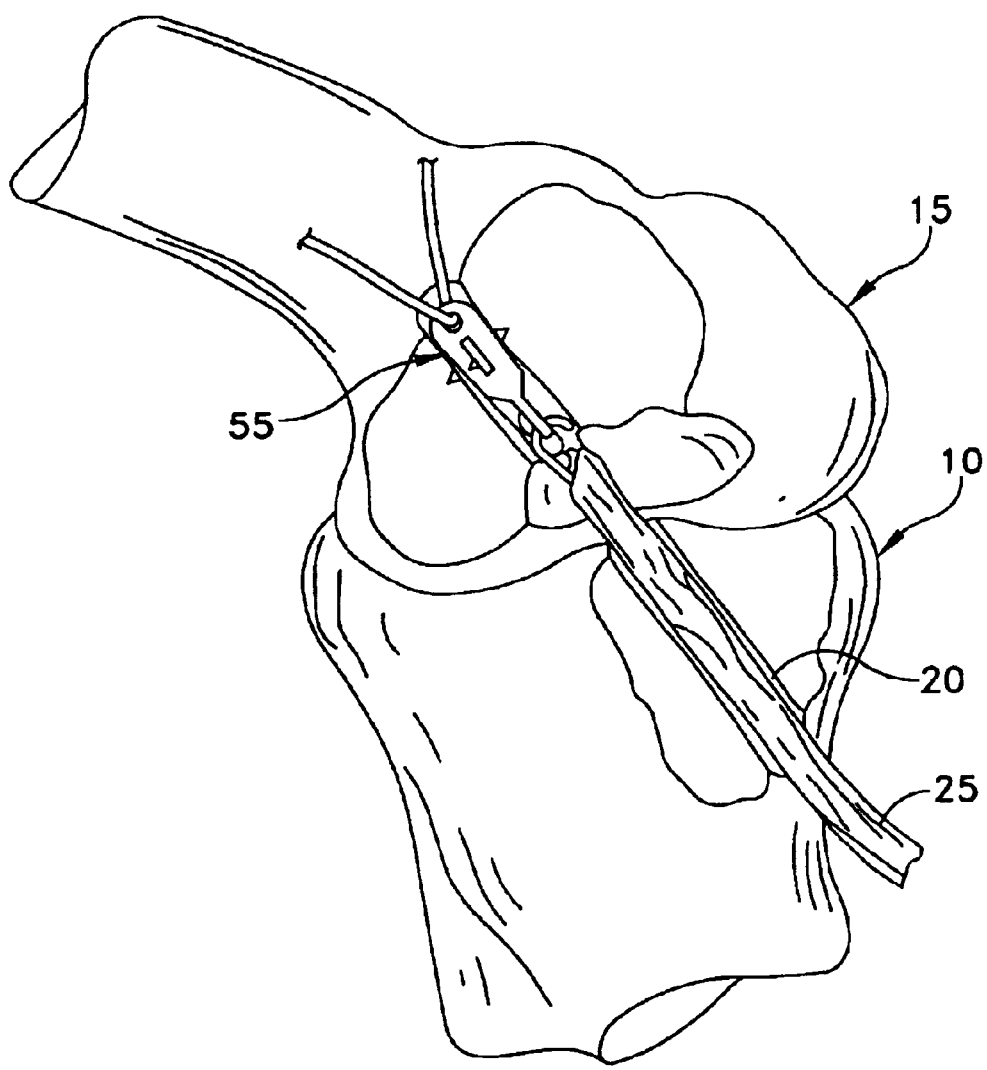
FIG. 6 is a schematic side elevational view showing a graft ligament secured in a bone tunnel by an anchor.
Figure 7:
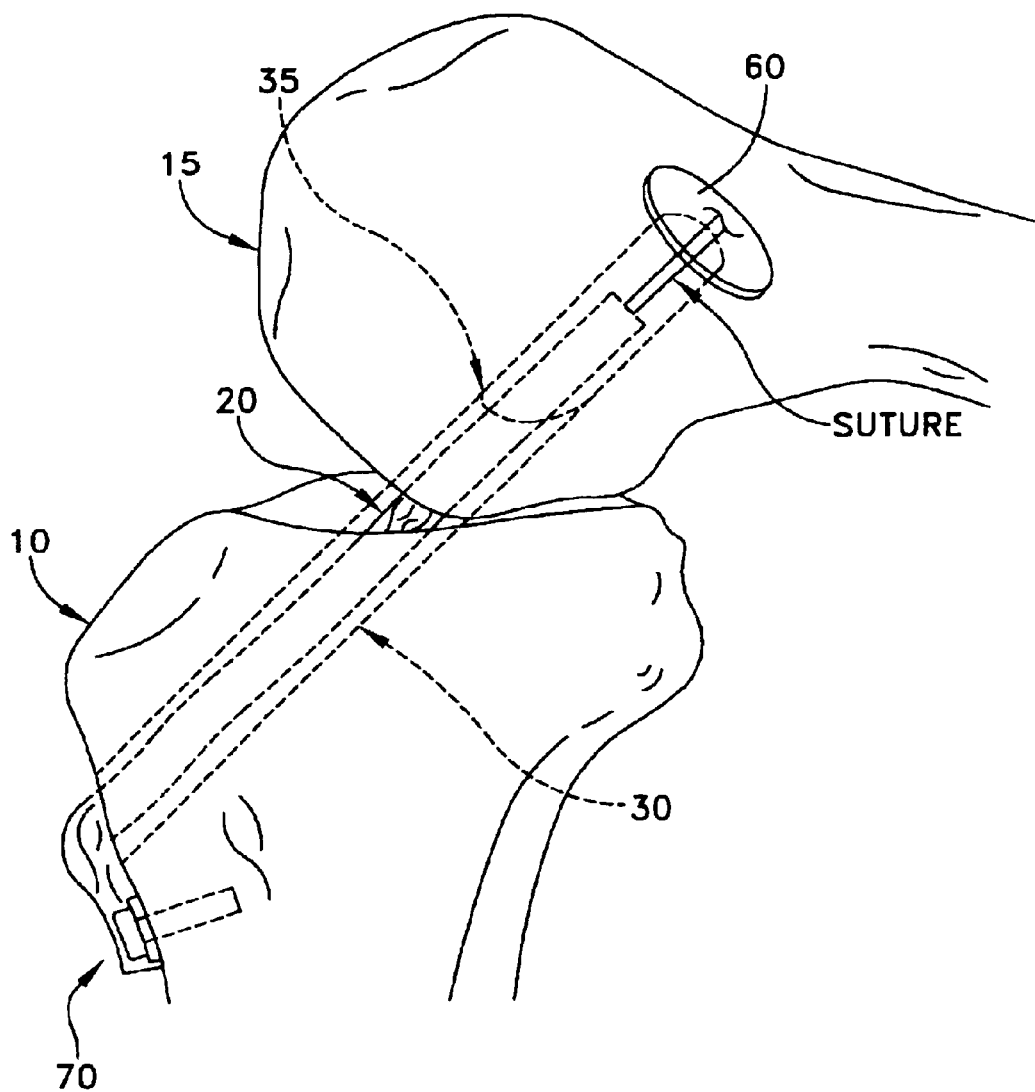
FIG. 7 is a schematic side elevational view showing a graft ligament secured in a bone tunnel by a suture suspension system.
Figure 8:
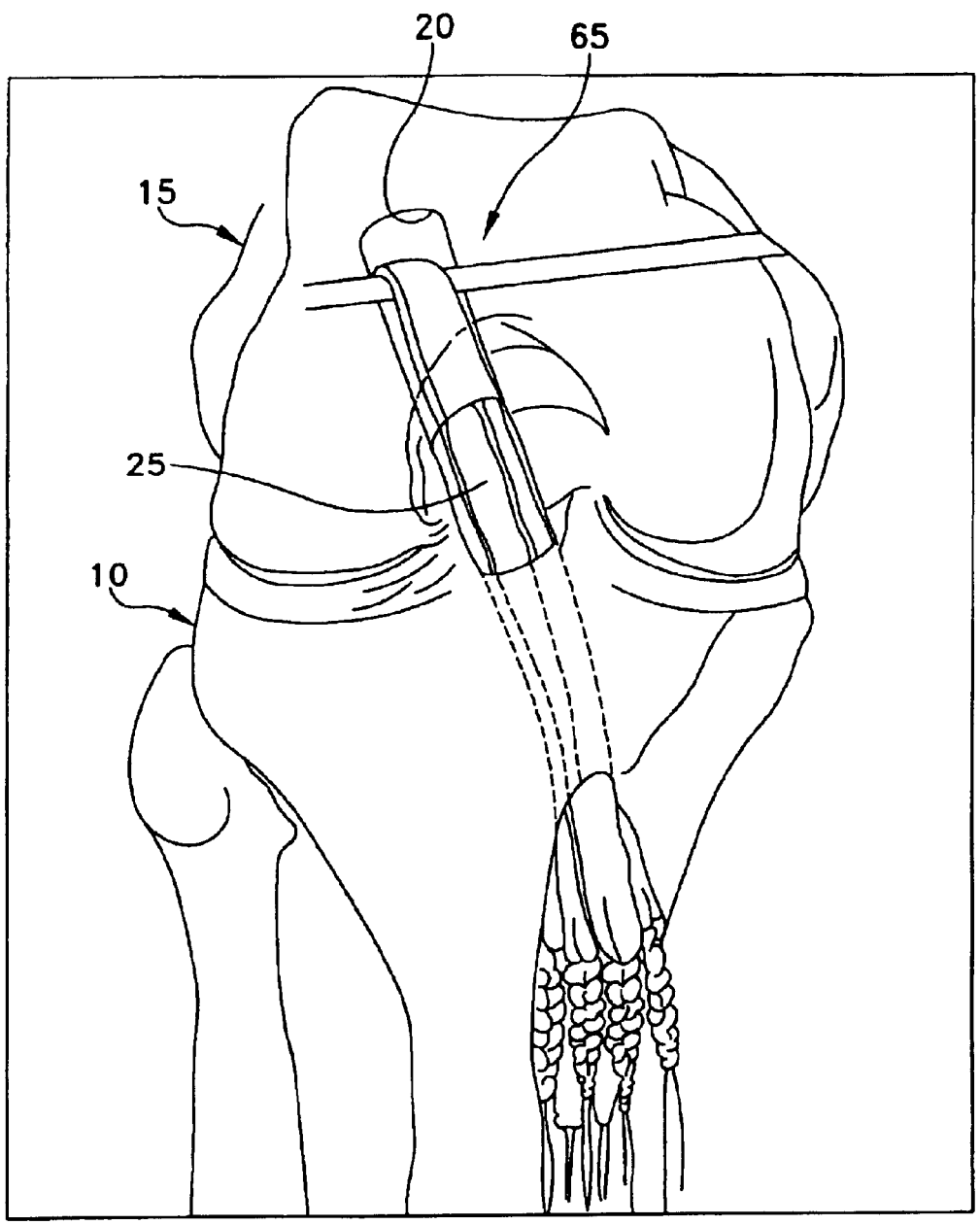
FIG. 8 is schematic side elevational view showing a graft ligament secured in a bone tunnel by a cross-pinning system.
Figure 9:
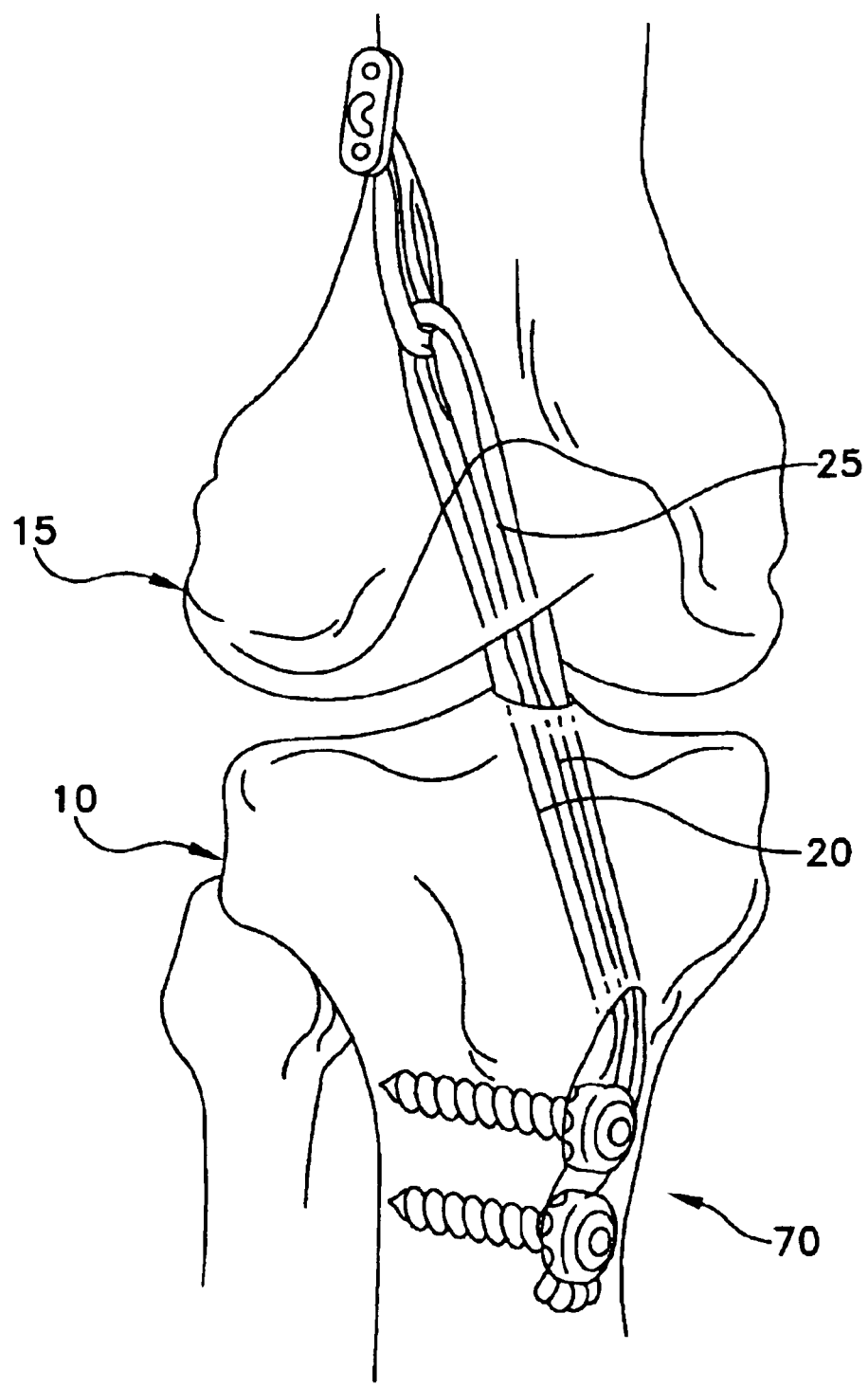
FIG. 9 is a schematic side elevational view showing a graft ligament secured in a bone tunnel a screw and washer arrangement.
Figure 10:
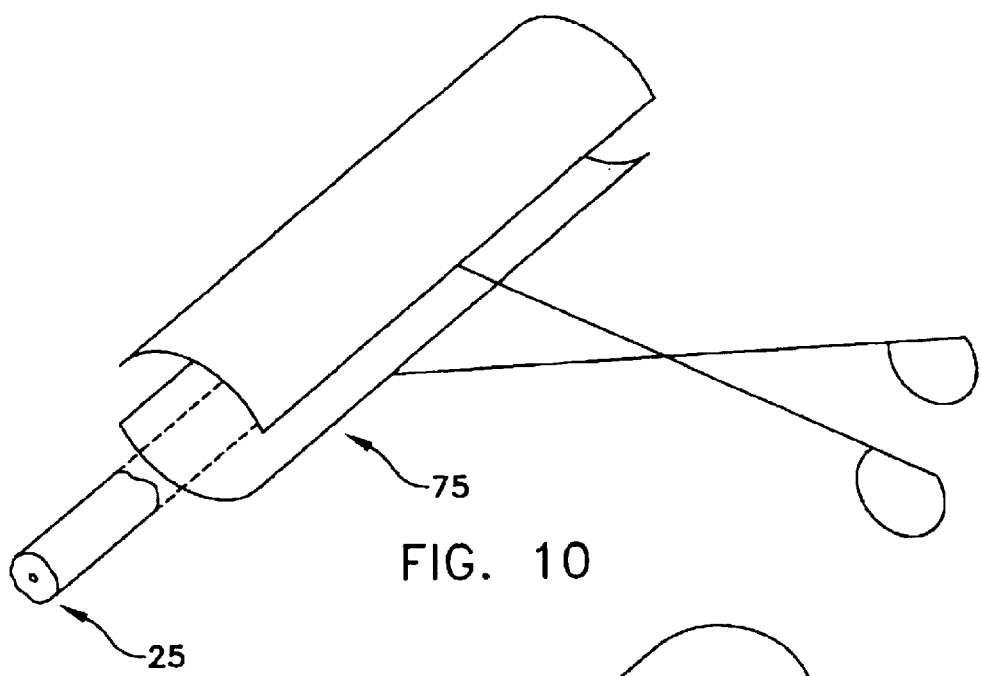
FIG. 10 is a schematic perspective view showing a pair of squeezing pliers for compacting a graft ligament.
Figure 11:
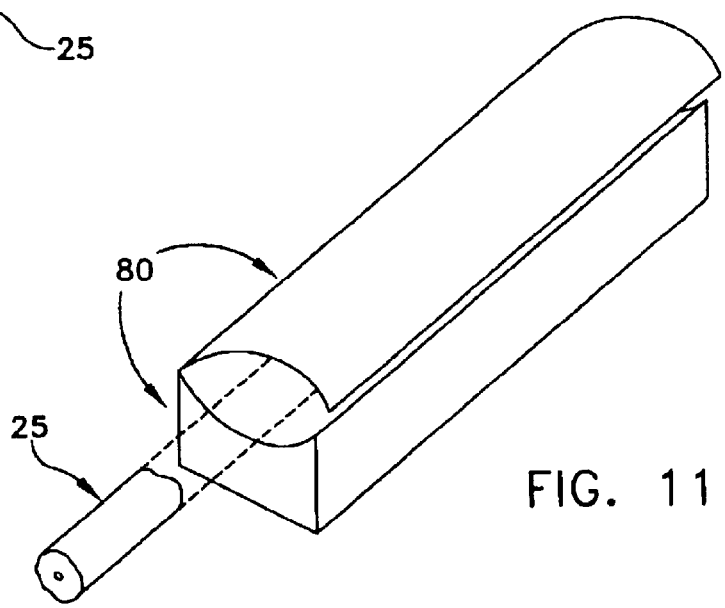
FIG. 11 is a schematic perspective view showing a pair of hinged plates for compacting a graft ligament.
Figure 13:
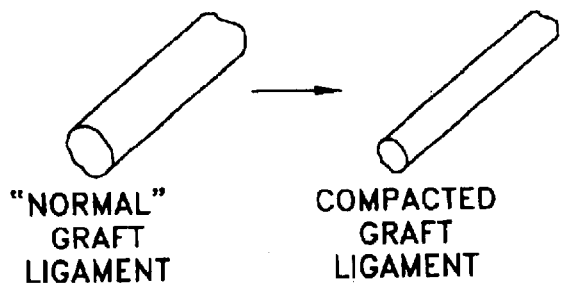
FIG. 13 is a schematic perspective view showing a comparison of a normal graft ligament and a compressed graft ligament.
Figure 12:
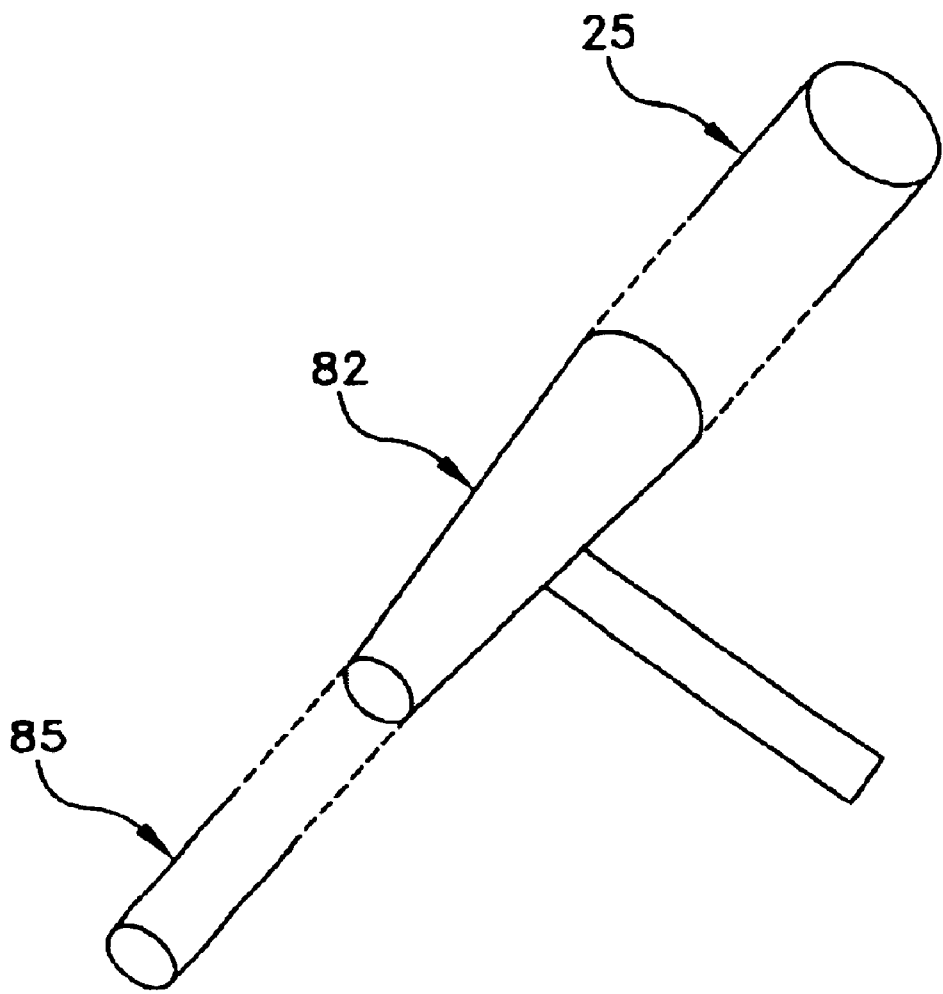
FIG. 12 is a schematic perspective view showing a conical tube for compacting a graft ligament.

Compaction can be effected using a variety of instruments, e.g., squeezing pliers 75 (FIG. 10), hinged plates 80 (FIG. 11), conical tube 82 (FIG. 12), etc. Such compaction will typically take less than 1 minute to achieve, and will typically reduce the width and height dimensions of graft ligament 25 by ½, thus resulting in a compressed graft ligament 85 having a cross-sectional area just ¼ of its original cross-sectional area (FIG. 13) without reducing its collagen content at all. In other words, by compacting the tendon, the size of the tendon can be decreased, thereby allowing a given tendon to be placed in a smaller, more precisely placed, and less-destructive bone hole. Or looked at another way, by compacting the tendon, a "larger" tendon (with more collagen material) can be fit into a given bone hole. Of course, compaction can be effected to varying degrees, permitting the surgeon to "size" a harvested hamstring tendon, or allograft, to a given patient's anatomical particulars. If desired, the compaction instruments (e.g., pliers 75, hinged plates 80, conical tube 82, etc.) can be configured so as to add contour to the tendon. For example, the pliers and/or hinged plates can have a "waffle iron" configuration, so as to provide a non-smooth surface configuration to the tendon. In addition, or in an alternative embodiment of the invention, the pliers and/or hinged plates can have one or two concave surfaces, so as to compact, and not flatten, the tendon. By way of example, the pliers and/or plates can comprise two concave surfaces so as to generate a circular or oval graft cross-section; or the pliers and/or plates can comprise one concave surface and one flat surface so as to generate a half-circular or half-oval graft cross-section.

In some cases, compressed tendon 85 may be able to be rehydrated in situ after it has been deployed in the knee, thereby swelling the tendon in situ and achieving a tighter fit with the walls of the bone tunnel 20. Rehydration can sometimes be achieved "naturally", e.g., by tendon 85 absorbing local fluids, or rehydration can sometimes be achieved "artificially", i.e., by introducing external fluids to tendon 85. Where possible, such rehydration will typically take less than 1 minute to achieve, although it may also occur over a substantially longer period of time. If desired, the aforementioned external fluids can be used just to restore bulk to tendon 85, or the external fluids can be medically active (e.g., the fluids can comprise an antibiotic or a growth promoter, etc.). The rehydration fluids can also be some combination of natural and artificial fluids.

Alternatively, the tendon can be stitched in its compacted state or size. This stitching (not shown) keeps the tendon in this compacted state even after it is exposed to fluid in the body.

Significant advantages are achieved by using this new ligament reconstruction technique. For one thing, compressed tendons 85 have a reduced "footprint" during the deployment portion of the procedure, so that a given tendon 85 can be put into smaller bone tunnels 20 (thus leading to reduced bone trauma) while still leaving plenty of room for ligament deployment, instrument manipulation, fixation device, etc. Alternatively, a larger tendon 85 can be placed in a given bone tunnel 20; since compressed tendon 85 retains all of its original collagen content, it (1) provides greater strength along its length, whereby to prevent subsequent rupture, and (2) provides an extensive supply of collagen material, whereby to facilitate effective integration of graft ligament 85 into the bone. Among other things, compressed ligament 85 can be ingrown by sharpey fibers more thoroughly and completely than non-compressed tendon 25. In addition, by using varying degrees of compression and/or varying geometries of compacting tools, a particular tendon 25 can be effectively sized or shaped to a given patient's anatomical particulars. And a compressed tendon 85, and especially a stitched compressed tendon (not shown), tends to be less susceptible to wrapping itself around a fixation screw than a non-compressed tendon 25. In addition, compressed tendons 85 have a reduced footprint which permits the use of smaller fixation devices (e.g., an interference screw), and a smaller range of fixation devices, thereby leading to smaller inventory needs. In addition, in some cases, tendons 85 may thereafter swell in situ, effectively filling the bone tunnel with their tissue mass. This swelling causes tendons 85 to come into compressive engagement with the surrounding walls of bone tunnel 20, such that the tendon cells and the bone tunnel cells are forced into close contact with one another. This results in enhanced biological ingrowth and thus a more stable repair.

In addition, swelling of tendons 85 in situ helps eliminate any harmful movement of tendons 85 within the bone tunnels, and also helps seal off bone tunnel 20 against any detrimental ingress of synnovial fluid.

What is claimed is:

1. A method for graft ligament reconstruction, the method comprising:
    (i) harvesting a graft ligament consisting entirely of soft tissue;
    (ii) dehydrating said graft ligament through compression, so as to significantly reduce the cross-sectional area and increase the density of the collagen material of said graft ligament;
    (iii) deploying said compressed graft ligament in a human body; and
    (iv) rehydrating said graft ligament in situ by introducing an external rehydration fluid to said graft ligament from outside of the human body.

2. The method of claim 1 wherein said graft ligament is an allograft tendon.

3. The method of claim 1 wherein said graft ligament is a hamstring tendon.

4. The method of claim 1 wherein said graft ligament is deployed in the knee.

5. The method of claim 1 wherein the step of compacting said graft ligament through compression includes using a compacting instrument.

6. The method of claim 5 wherein said compacting instrument is a pair of squeezing pliers.

7. The method of claim 5 wherein said compacting instrument is a pair of hinged plates.

8. The method of claim 5 wherein said compacting instrument is a conically shaped tube.

9. The method of claim 1 further comprising the step of suturing the compressed ligament so as to hold said graft ligament in its compacted state and to reinforce said graft ligament against damage.

10. The method of claim 1 further comprising the step of providing a non-smooth surface configuration to at least a portion of said graft ligament.

11. The method of claim 1 wherein the external rehydration fluid comprises a natural fluid.

12. The method of claim 1 wherein the external rehydration fluid comprises an artificial fluid.

13. The method of claim 1 wherein the external rehydration fluid comprises a combinatton of natural and artificial fluids.

14. The method of claim 1 wherein the external rehydration fluid comprises a medically active fluid.

15. The method of claim 14 wherein the medically active fluid comprises an antibiotic drug.

16. The method of claim 14 wherein the medically active fluid comprises a growth promoting drug.

* * * * *